(12) United States Patent
Ye et al.

(10) Patent No.: US 11,105,742 B2
(45) Date of Patent: Aug. 31, 2021

(54) NUCLEATED RED BLOOD CELL WARNING METHOD AND DEVICE, AND FLOW CYTOMETER USING THE SAME

(71) Applicant: Shenzhen Mindray Bio-Medical Electronics Co., Ltd., Shenzhen (CN)

(72) Inventors: Bo Ye, Shenzhen (CN); Huan Qi, Shenzhen (CN); Cheng Qian, Shenzhen (CN)

(73) Assignee: Shenzhen Mindray Bio-Medical Electronics Co., Ltd., Shenzhen (CN)

( * ) Notice: Subject to any disclaimer, the term of this patent is extended or adjusted under 35 U.S.C. 154(b) by 461 days.

(21) Appl. No.: 15/638,902

(22) Filed: Jun. 30, 2017

(65) Prior Publication Data

US 2018/0003634 A1 Jan. 4, 2018

Related U.S. Application Data

(63) Continuation of application No. PCT/CN2014/095905, filed on Dec. 31, 2014.

(51) Int. Cl.
*G01N 21/64* (2006.01)
*G01N 33/49* (2006.01)
(Continued)

(52) U.S. Cl.
CPC ......... *G01N 21/64* (2013.01); *G01N 15/1459* (2013.01); *G01N 33/49* (2013.01); *G01N 2015/0076* (2013.01)

(58) Field of Classification Search
CPC ................................ G01N 21/64; G01N 33/49
(Continued)

(56) References Cited

U.S. PATENT DOCUMENTS 4,751,179 A * 6/1988 Ledis ..................... G01N 33/48
435/34
4,882,284 A * 11/1989 Kirchanski ........ G01N 15/1456
436/63
(Continued)

FOREIGN PATENT DOCUMENTS

CN         1844922 A     10/2006
CN    101236194 A      8/2008
(Continued)

*Primary Examiner* — Arlen Soderquist
(74) *Attorney, Agent, or Firm* — Kory D. Christensen

(57) ABSTRACT

Disclosed are nucleated red blood cell warning devices and methods, and flow cytometers using the same. The devices, methods and flow cytometers can warn whether nucleated red blood cells exist in a blood sample. The warning device may obtain forward-scattered light information, side-scattered light information and fluorescence information when cells in the blood sample pass through a detection region of the flow cytometer. The warning device may generate a side-scattered light-fluorescence dot plot, so as to classify leucocytes into four groups, and may generate a forward-scattered light-fluorescence dot plot, where the forward-scattered light-fluorescence dot plot can include a leucocyte group region. The warning device may obtain a predetermined feature region located at the left side of the leucocyte group region, perform statistics on the amount of characterization cells in the predetermined feature region, and provide a warning when the number of the characterization cells exceeds a threshold value.

24 Claims, 6 Drawing Sheets

(51) Int. Cl.
*G01N 15/14* (2006.01)
*G01N 15/00* (2006.01)

(58) Field of Classification Search
USPC .................................. 422/81; 436/52, 63
See application file for complete search history.

(56) References Cited

U.S. PATENT DOCUMENTS

| | | | | |
|---|---|---|---|---|
| 5,264,369 A * | 11/1993 | Sakata | ............... | G01N 15/147 436/17 |
| 5,298,426 A * | 3/1994 | Inami | ............... | G01N 15/1456 435/6.11 |
| 5,308,772 A * | 5/1994 | Sakata | ............... | G01N 33/5094 436/17 |
| 5,413,938 A * | 5/1995 | Tsujino | ............... | G01N 33/5094 436/63 |
| 5,496,734 A * | 3/1996 | Sakata | ............... | G01N 33/5094 435/2 |
| 5,516,695 A * | 5/1996 | Kim | ............... | C12N 1/06 435/2 |
| 5,518,928 A * | 5/1996 | Cremins | ............... | G01N 33/5094 436/10 |
| 5,559,037 A * | 9/1996 | Kim | ............... | G01N 15/1456 356/317 |
| 5,618,733 A * | 4/1997 | Sakata | ............... | G01N 33/5002 436/17 |
| 5,631,165 A * | 5/1997 | Chupp | ............... | B01F 5/0453 422/63 |
| 5,648,225 A * | 7/1997 | Kim | ............... | C12N 1/06 424/154.1 |
| 5,821,127 A * | 10/1998 | Akai | ............... | C09B 23/02 436/10 |
| 5,874,310 A * | 2/1999 | Li | ............... | G01N 33/80 436/10 |
| 5,905,031 A * | 5/1999 | Kuylen | ............... | C12Q 1/26 435/29 |
| 6,004,816 A | 12/1999 | Mizukami et al. | | |
| 6,365,106 B1 * | 4/2002 | Nagai | ............... | G01N 15/1404 356/246 |
| 6,551,831 B2 * | 4/2003 | Gupta | ............... | C09B 23/02 252/408.1 |
| 6,664,110 B1 * | 12/2003 | Tsuji | ............... | G01N 33/5094 436/10 |
| 2002/0006631 A1 * | 1/2002 | Houwen | ............... | G01N 15/1459 435/7.24 |
| 2002/0086344 A1 * | 7/2002 | Tsuji | ............... | G01N 33/5002 435/29 |
| 2003/0025896 A1 * | 2/2003 | Oever | ............... | G01N 15/1456 356/39 |
| 2003/0030784 A1 * | 2/2003 | Narisada | ............... | G01N 15/1456 356/39 |
| 2003/0032193 A1 * | 2/2003 | Narisada | ............... | G01N 15/1459 436/63 |
| 2003/0143117 A1 * | 7/2003 | Nagai | ............... | G01N 15/1459 422/73 |
| 2003/0219850 A1 * | 11/2003 | Tsuji | ............... | G01N 1/30 435/40.5 |
| 2003/0235917 A1 * | 12/2003 | Li | ............... | G01N 15/12 436/10 |
| 2004/0018629 A1 * | 1/2004 | Kawate | ............... | G01N 15/1468 436/63 |
| 2004/0189977 A1 * | 9/2004 | Nagai | ............... | G01N 15/1459 356/39 |
| 2004/0241770 A1 * | 12/2004 | Houwen | ............... | G01N 33/5094 435/7.21 |
| 2005/0176152 A1 * | 8/2005 | Lopez | ............... | G01N 15/12 436/63 |
| 2006/0040291 A1 * | 2/2006 | Dertinger | ............... | G01N 1/30 435/6.14 |
| 2006/0160229 A1 * | 7/2006 | Lopez | ............... | G01N 15/12 436/63 |
| 2006/0250604 A1 * | 11/2006 | Hamada | ............... | G01N 15/1459 356/39 |
| 2007/0020721 A1 * | 1/2007 | Yoshida | ............... | G01N 15/1459 435/34 |
| 2007/0231913 A1 * | 10/2007 | Tsuji | ............... | G01N 15/1459 436/63 |
| 2007/0287145 A1 * | 12/2007 | Mizukami | ............... | G01N 33/5094 435/4 |
| 2007/0298408 A1 * | 12/2007 | Mizukami | ............... | G01N 33/5094 435/4 |
| 2008/0024759 A1 * | 1/2008 | Ikeuchi | ............... | G01N 15/1459 356/40 |
| 2008/0153170 A1 * | 6/2008 | Garrett | ............... | G01N 15/147 436/63 |
| 2008/0180653 A1 * | 7/2008 | Narisada | ............... | G01N 15/12 356/36 |
| 2008/0187951 A1 * | 8/2008 | Nagai | ............... | G01N 15/12 435/29 |
| 2008/0187990 A1 * | 8/2008 | Nagai | ............... | G01N 15/12 435/286.1 |
| 2008/0194508 A1 * | 8/2008 | Christensen | ............... | G01N 15/1459 514/44 R |
| 2008/0311586 A1 * | 12/2008 | Dertinger | ............... | G01N 33/5094 435/6.12 |
| 2009/0023129 A1 * | 1/2009 | Xu | ............... | G01N 15/1459 435/2 |
| 2009/0035758 A1 * | 2/2009 | Wolfers | ............... | C12Q 1/6806 435/6.11 |
| 2009/0323062 A1 * | 12/2009 | Ariyoshi | ............... | G16H 10/40 356/337 |
| 2010/0112584 A1 * | 5/2010 | Shao | ............... | C07D 403/08 435/6.12 |
| 2010/0143955 A1 * | 6/2010 | Baohua | ............... | G01N 33/5094 435/14 |
| 2010/0184061 A1 * | 7/2010 | Kataoka | ............... | G01N 33/56972 435/6.12 |
| 2010/0248247 A1 * | 9/2010 | Kataoka | ............... | G01N 33/49 435/6.1 |
| 2010/0248300 A1 * | 9/2010 | Yoshida | ............... | G01N 15/1459 435/39 |
| 2010/0267080 A1 * | 10/2010 | Kuang | ............... | C09K 11/06 435/39 |
| 2010/0273168 A1 * | 10/2010 | Krockenberger | ............... | G01N 15/00 435/6.12 |
| 2010/0330565 A1 * | 12/2010 | Narikawa | ............... | G01N 21/6428 435/6.11 |
| 2011/0027788 A1 * | 2/2011 | Zhao | ............... | G01N 33/56972 435/6.16 |
| 2011/0045525 A1 * | 2/2011 | Krockenberger | ............... | G01N 15/1459 435/34 |
| 2011/0077870 A1 * | 3/2011 | Linssen | ............... | G01N 15/147 702/19 |
| 2011/0159483 A1 * | 6/2011 | Zhao | ............... | C07D 209/12 435/4 |
| 2011/0159535 A1 * | 6/2011 | Deng | ............... | G01N 21/6428 435/34 |
| 2011/0275064 A1 * | 11/2011 | Wu | ............... | G01N 15/147 435/6.1 |
| 2012/0282599 A1 * | 11/2012 | Wu | ............... | G01N 15/1434 435/6.1 |
| 2012/0282601 A1 * | 11/2012 | Abe | ............... | G01N 35/026 435/6.1 |
| 2014/0011232 A1 * | 1/2014 | Vidal | ............... | C12Q 1/06 435/39 |
| 2014/0051071 A1 * | 2/2014 | Yoshida | ............... | G01N 21/51 435/6.1 |
| 2015/0276720 A1 * | 10/2015 | Abe | ............... | G01N 33/5094 435/29 |
| 2017/0315046 A1 * | 11/2017 | Du | ............... | G01N 21/6428 |

FOREIGN PATENT DOCUMENTS

| | | |
|---|---|---|
| CN | 101750476 A | 6/2010 |
| CN | 101086473 B | 9/2010 |
| CN | 101846671 A | 9/2010 |

(56) References Cited

FOREIGN PATENT DOCUMENTS

| | | | |
|---|---|---|---|
| CN | 102033122 A | | 4/2011 |
| CN | 103492875 A | | 1/2014 |
| JP | 10-339729 | * | 12/1998 |

* cited by examiner

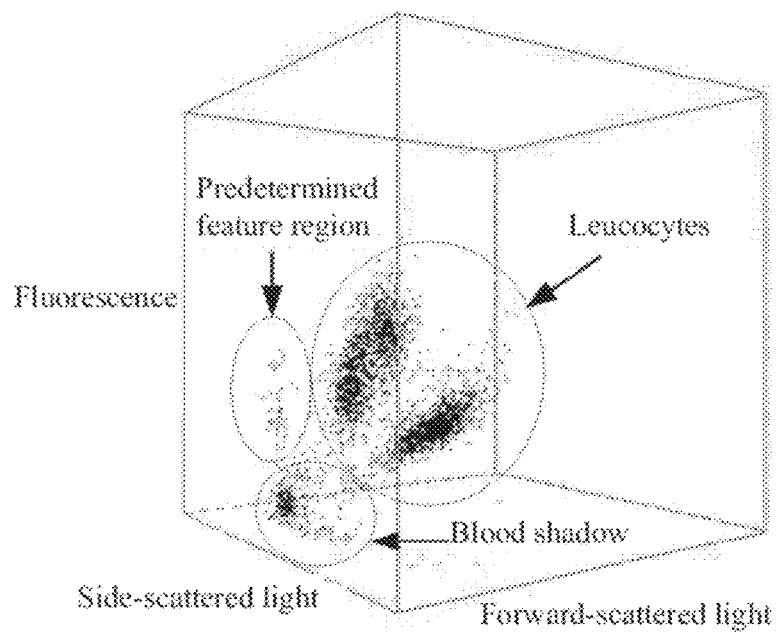
FIG. 4
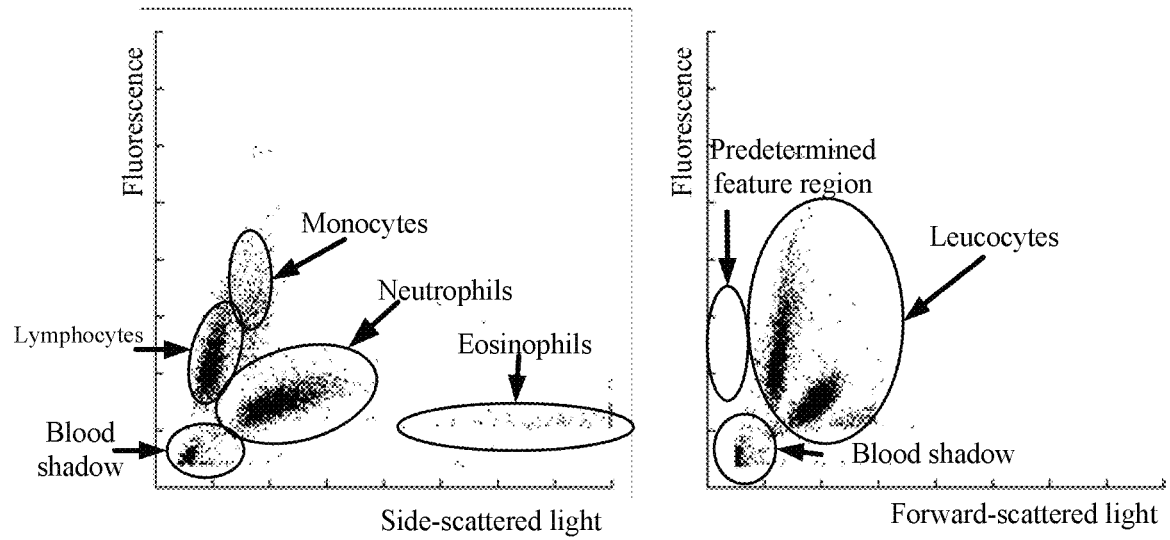
Fig. 5A
Fig. 5B

NUCLEATED RED BLOOD CELL WARNING METHOD AND DEVICE, AND FLOW CYTOMETER USING THE SAME

CROSS-REFERENCE TO RELATED APPLICATIONS

This application is a continuation of Patent Cooperation Treaty Application No. PCT/CN2014/095905, filed Dec. 31, 2014, which is hereby incorporated by reference.

TECHNICAL FIELD

This disclosure relates to the field of medical devices, and more particularly relates to a nucleated red blood cell warning method and device and a flow cytometer.

SUMMARY

This disclosure provides a nucleated red blood cell warning method and device and a flow cytometer, which are able to provide warning for nucleated red blood cells while classifying and detecting leucocytes.

BRIEF DESCRIPTION OF THE DRAWINGS

In order to more clearly illustrate technical solutions in the embodiments of this disclosure or in the prior art, a brief introduction to the drawings required for the description of the embodiments or the prior art will be provided below. It may be understood that the drawings described below are only some of the embodiments of this disclosure, and those of ordinary skilled persons in the art would also be able to obtain other drawings from these drawings without expending any inventive effort.

FIG. 4 is a schematic diagram of a three-dimensional dot plot corresponding to FIG. 3A and FIG. 3B;

FIG. 5A is a schematic diagram of a side-scattered light-fluorescence dot plot corresponding to a blood sample containing no nucleated red blood cells;

FIG. 5B is a schematic diagram of a forward-scattered light-fluorescence dot plot corresponding to a blood sample containing no nucleated red blood cells;

DETAILED DESCRIPTION

Figure 1:
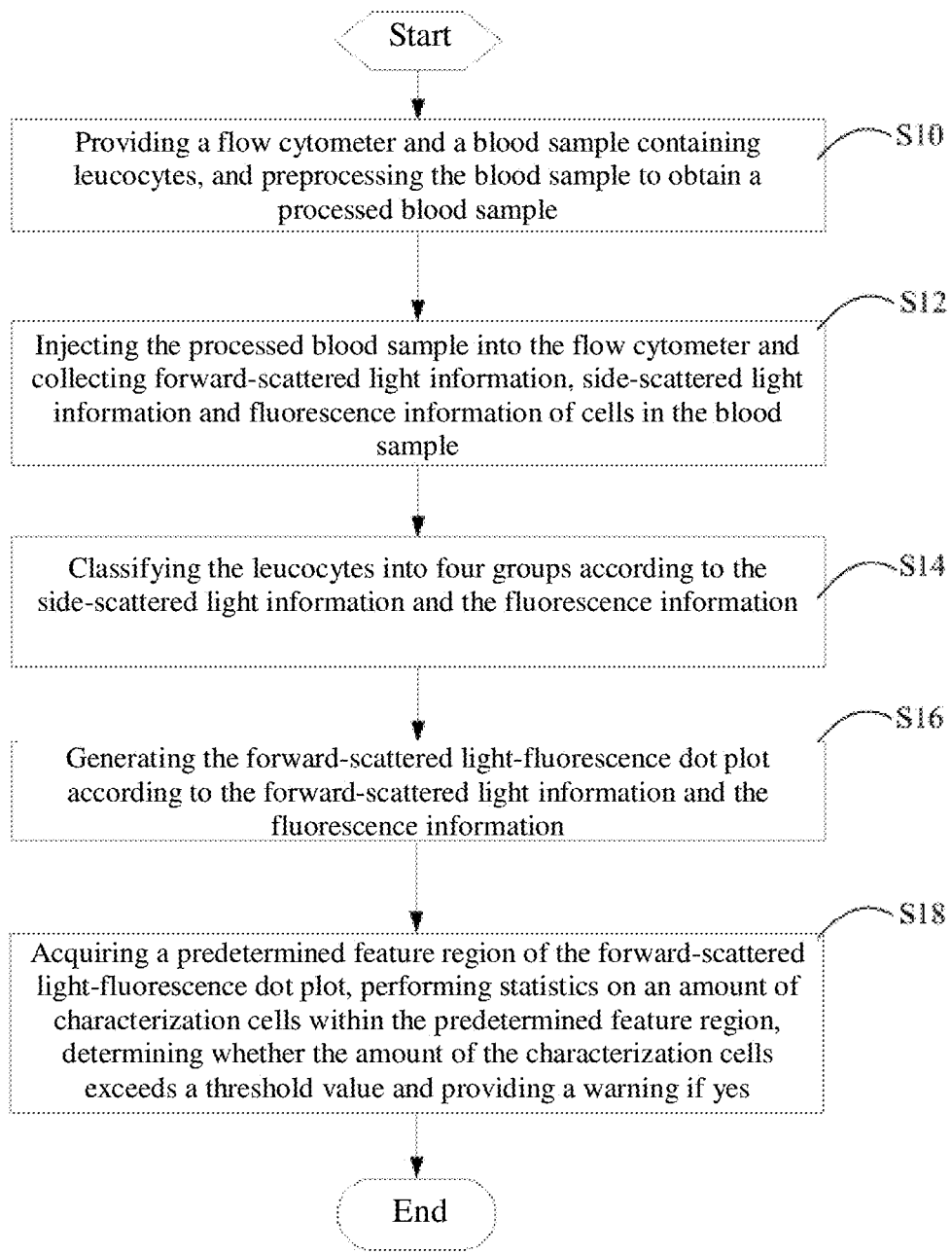
FIG. 1 is a flowchart of a nucleated red blood cell warning method.

The technical solutions of the embodiments of this disclosure will be described below clearly and comprehensively in conjunction with the drawings of the embodiments of this disclosure. It may be understood that the embodiments described are merely some embodiments rather than all the possible embodiments of this disclosure. Based on the embodiments given in this disclosure, other embodiments that would be obtained by those of ordinary skilled persons in the art without expending inventive effort shall all fall within the scope of protection of this disclosure.

Below the embodiments of this disclosure are described with reference to the drawings.

Some of the terms used in the descriptions are defined below.

The word "dot plot" may refer to a two-dimensional diagram that is generated by a flow cytometer and contains two-dimensional feature information about a plurality of particles distributed thereon, where an X coordinate axis and a Y coordinate axis of the dot plot represent a respective feature of each particle. For example, in a dot plot, the X coordinate axis may represent forward-scattered light intensity, and the Y coordinate axis may represent fluorescence intensity.

The word "cell population" may refer to a particle cluster that is distributed in a region of a dot plot and is formed by a plurality of particles having substantially same features. For example, the cell population can be a leucocyte population, or can be a neutrophil population, a lymphocyte population, a monocyte population, an eosinophil population or a basophil population among leucocytes.

Nucleated red blood cells (NRBCs) may refer to immature red blood cells, which are normally present in bone marrow, and therefore nucleated red blood cells may not appear in a normal human blood sample (blood other than bone marrow). Nucleated red blood cells appear in a blood sample due to immature bone marrow erythroid cells being released into the blood sample, and their appearance in the blood sample can be associated with a blood disease. Therefore, there is a clinical need to detect whether nucleated red blood cells exist in the blood.

Recently, flow cytometers which use flow cytometry counting principles to count and classify blood cells have come out one after another. Due to their simple, convenient and fast operation and high level of accuracy and precision of results, they have greatly promoted the development of blood detection technology and provided more diagnostic information for clinical medicine. The flow cytometer may receive photoelectric signals produced by laser irradiation of cells, and then present the photoelectric signals produced by the laser irradiation of cells, e.g., as a dot plot, for further analysis. A scattered light signal and a fluorescence signal thereof reflect physicochemical features of the cells, such as the size, granularity and the expression of antigen molecules of the cells.

For the flow cytometers, some methods such as electrical impedance method and laser scattering method can be used for classification and counting of leucocytes. These methods may first hemolyze red blood cells in a blood sample, and then pass the blood sample to be detected through a detector, so as to classify leucocytes into several groups according to a difference in electrical signals or optical signals of the leucocytes, for example into neutrophils, lymphocytes, monocytes, eosinophils or basophils.

During the detection of the leucocytes, the presence of nucleated red blood cells may interfere with a leucocyte measurement result. In the aforementioned measurement methods, signals acquired in the detection of nucleated red blood cells and lymphocytes are similar to each other and not easy to distinguish. In this way, first the counting and classification of leucocytes may be affected, and furthermore, if it is not possible to highlight that nucleated red blood cells may exist in a sample, this will lead to a missed diagnosis, thereby losing treatment opportunities for the disease.

In order to detect nucleated red blood cells, a specialized detection reagent and method may be used aiming at the nucleated red blood cell. Although this method by using specialized reagent system and detection device can count the nucleated red blood cells, it may lead to increased volume and complexity of detection instruments, and the costs of clinical examination may also be increased.

In some embodiments, a nucleated red blood cell warning method may be provided for warning whether nucleated red blood cells exist in a blood sample. Forward-scattered light information, side-scattered light information and fluorescence information of cells may be acquired when the cells in the blood sample pass through a detection region of a flow cytometer. According to the side-scattered light information and the fluorescence information, leucocytes in the blood sample may be classified into at least four groups: a lymphocyte population, a monocyte population, an eosinophil population, and a neutrophil and basophil population. According to the forward-scattered light information and the fluorescence information, a forward-scattered light-fluorescence dot plot of the blood sample may be generated, where the forward-scattered light-fluorescence dot plot may include a leucocyte population region. A predetermined feature region of the forward-scattered light-fluorescence dot plot may then be acquired, and statistics may be performed on an amount of characterization cells in the predetermined feature region. It may then determine whether the amount of the characterization cells exceeds a predetermined threshold value, and a warning may be provided when it is determined that the amount of the characterization cells exceeds the predetermined threshold value. Here, the predetermined feature region is located at a left side of the leucocyte population region.

In some embodiments, the amount of the characterization cells in the predetermined feature region may be counted, and the counted amount of the characterization cells may be compared with the predetermined threshold value. When the amount of the characterization cells is greater than the predetermined threshold value, it may determine that nucleated red blood cells exist in the blood sample, and a warning may then be provided.

In some embodiments, the forward-scattered light-fluorescence dot plot may be analyzed and a region located at the left side of the leucocyte population region and at an upper side of a blood shadow region in the forward-scattered light-fluorescence dot plot can be determined as the predetermined feature region.

In some embodiments, the forward-scattered light information, the side-scattered light information and the fluorescence information of the cells in the blood sample may be acquired from detection data obtained from a single channel.

In some embodiments, the warning may include providing a warning prompt in a form of text, sound, light or pop-up window.

In some embodiments, a nucleated red blood cell warning device may be provided for warning whether nucleated red blood cells exist in a blood sample. The nucleated red blood cell warning device may include a processor. The processor may acquire forward-scattered light information, side-scattered light information and fluorescence information when cells in the blood sample pass through a detection region of a flow cytometer. The processor may generate a side-scattered light-fluorescence dot plot according to the side-scattered light information and the fluorescence information and classify leucocytes in the blood sample into at least four groups: a lymphocyte population, a monocyte population, an eosinophil population, and a neutrophil and basophil population. The processor may generate a forward-scattered light-fluorescence dot plot of the blood sample according to the forward-scattered light information and the fluorescence information, where the forward-scattered light-fluorescence dot plot may include a leucocyte population region. The processor may acquire a predetermined feature region of the forward-scattered light-fluorescence dot plot, perform statistics on an amount of characterization cells in the predetermined feature region, determine whether the amount of the characterization cells exceeds a predetermined threshold value, and provide a warning when it is determined that the amount of the characterization cells exceeds the predetermined threshold value, where the predetermined feature region is located at a left side of the leucocyte population region.

In some embodiments, the processor may analyze the forward-scattered light-fluorescence dot plot and determine a region located at the left side of the leucocyte population region and at an upper side of a blood shadow region in the forward-scattered light-fluorescence dot plot as the predetermined feature region.

In some embodiments, the processor may count the amount of the characterization cells in the predetermined feature region, compare the amount of the characterization cells with the predetermined threshold value, determine that nucleated red blood cells exist in the blood sample when the amount of the characterization cells is greater than the predetermined threshold value, and provide the warning when it is determined that nucleated red blood cells exist in the blood sample.

In some embodiments, the processor may acquire the forward-scattered light information, the side-scattered light information and the fluorescence information of the cells in the blood sample from detection data obtained from a single channel.

In some embodiments, a flow cytometer may be provided. The flow cytometer may include a sampling device, a preprocessing device, a detection device and analysis device. The sampling device may draw a blood sample, where the blood sample may contain at least leucocytes. The preprocessing device may preprocess the blood sample to obtain a processed blood sample, where the preprocessing may include performing fluorescence labeling on cells in the blood sample. The detection device may cause the cells in the processed blood sample to pass through a detection region one by one, and detect forward-scattered light information, side-scattered light information and fluorescence information of the cells in the processed blood sample. The analysis device may generate a forward-scattered light-fluorescence dot plot of the blood sample according to the forward-scattered light information and the fluorescence information detected by the detection device, acquire a predetermined feature region of the forward-scattered light-fluorescence dot plot, perform statistics on an amount of characterization cells in the predetermined feature region, determine whether the amount of the characterization cells exceeds a predetermined threshold value, and provide a warning when it is determined that the amount of the characterization cells exceeds the predetermined threshold value, where the forward-scattered light-fluorescence dot plot may include a leucocyte population region and the predetermined feature region is located at a left side of the leucocyte population region.

In some embodiments, the analysis device may acquire the forward-scattered light information, the side-scattered light information and the fluorescence information when the cells in the processed blood sample pass through the detection region of said flow cytometer. The analysis device may generate a side-scattered light-fluorescence dot plot according to the acquired side-scattered light information and the acquired fluorescence information, classify the leucocytes of the blood sample into at least four groups: a lymphocyte population, a monocyte population, an eosinophil population, and a neutrophil and basophil population, and generate the forward-scattered light-fluorescence dot plot of the blood sample according to the acquired forward-scattered light information and the acquired fluorescence information, where the forward-scattered light-fluorescence dot plot may include the leucocyte population region. The analysis device may acquire the predetermined feature region of the forward-scattered light-fluorescence dot plot, perform statistics on the amount of the characterization cells in the predetermined feature region, determine whether the amount of the characterization cells exceeds the predetermined threshold value, and provide the warning when it is determined that the amount of the characterization cells exceeds the predetermined threshold value, where the predetermined feature region is located at the left side of the leucocyte population region.

The analysis device may analyze the forward-scattered light-fluorescence dot plot and determine a region located at the left side of the leucocyte population region and at an upper side of a blood shadow region in the forward-scattered light-fluorescence dot plot as the predetermined feature region.

In some embodiments, the detection device may detect and collect the forward-scattered light information, the side-scattered light information and the fluorescence information of the cells in the blood sample using a single channel.

In some embodiments, a nucleated red blood cell warning method may be provided for warning whether nucleated red blood cells exist in a blood sample. The method may include steps below.

A flow cytometer and a blood sample may be provided, where the blood sample may include leucocytes.

The blood sample may be preprocessed so as to obtain a processed blood sample, where the preprocessing may include performing fluorescent labeling on cells in the blood sample.

The processed blood sample may be injected into the flow cytometer, and forward-scattered light information, side-scattered light information and fluorescence information of the cells may be collected.

According to the side-scattered light information and the fluorescence information, the leucocytes may be classified into at least four groups: a lymphocyte population, a monocyte population, an eosinophil population, and a neutrophil and basophil population.

According to the forward-scattered light information and the fluorescence information, a forward-scattered light-fluorescence dot plot of the blood sample may be generated, where the forward-scattered light-fluorescence dot plot may include a leucocyte population region.

A predetermined feature region of the forward-scattered light-fluorescence dot plot may be acquired, and statistics may be performed on an amount of characterization cells in the predetermined feature region. It may then determine whether the amount of the characterization cells exceeds a predetermined threshold value, and a warning may be provided when it is determined that the amount of the characterization cells exceeds the predetermined threshold value, where the predetermined feature region is located at a left side of the leucocyte population region.

In some embodiments, the amount of the characterization cells in the predetermined feature region may be counted, and the counted amount of the characterization cells may be compared with the predetermined threshold value. When the amount of the characterization cells is greater than the predetermined threshold value, it may determine that nucleated red blood cells exist in the blood sample, and a warning may then be provided.

In some embodiments, the forward-scattered light information, the side-scattered light information and the fluorescence information of the cells in the blood sample may be simultaneously collected when the cells pass through the detection region of the flow cytometer.

In some embodiments, the forward-scattered light-fluorescence dot plot may be analyzed and a region located at the left side of the leucocyte population region and at an upper side of a blood shadow region in the forward-scattered light-fluorescence dot plot may be determined as the predetermined feature region.

In some embodiments, a normal blood sample and an abnormal blood sample may be respectively provided. The normal blood sample may contain at least leucocytes, and the abnormal blood sample may contain at least leucocytes and nucleated red blood cells. The normal blood sample and the abnormal blood sample may be preprocessed so as to obtain a processed normal blood sample and a processed abnormal blood sample, where the preprocessing may include respectively performing fluorescent labeling on cells in the normal blood sample and the abnormal blood sample. The processed normal blood sample and the processed abnormal blood sample may be respectively injected into the flow cytometer, such that the forward-scattered light information, the side-scattered light information and the fluorescence information of the cells respectively in the processed normal blood sample and the processed abnormal blood sample may be collected. According to the side-scattered light information and the fluorescence information, the leucocytes respectively in the processed normal blood sample and the processed abnormal blood sample may be classified into at least four groups: a lymphocyte population, a monocyte population, an eosinophil population, and a neutrophil and basophil population. According to the forward-scattered light information and the fluorescence information, a forward-scattered light-fluorescence dot plot of the processed normal blood sample and a forward-scattered light-fluorescence dot plot of the processed abnormal blood sample may be generated. The forward-scattered light-fluorescence dot plot of the processed normal blood sample may be compared with the forward-scattered light-fluorescence dot plot of the processed abnormal blood sample so as to determine a region where a particle population appears at the left side of a leucocyte population region in the forward-scattered light-fluorescence dot plot of the processed abnormal blood sample and where no particle population appears at the left side of a leucocyte population region in the forward-scattered light-fluorescence dot plot of the processed normal blood sample, as the predetermined feature region.

FIG. 1 shows a main flowchart of a nucleated red blood cell warning method provided in one embodiment of this disclosure. In this embodiment, the nucleated red blood cell warning method can be used for warning whether nucleated red blood cells exist in a blood sample. The method may include some steps below.

At step S10, a flow cytometer and a blood sample containing leucocytes may be provided, where the blood sample may be preprocessed to obtain a processed blood sample. In some examples, the blood sample may be mixed in proportion with a reagent containing a fluorescent dye and a hemolytic component to form the processed blood sample. The reagent here may be used to hemolyze red blood cells in the blood sample, so as to avoid interference to the counting of the leucocytes and the nucleated red blood cells. Also, the fluorescent dye in the reagent may bind with nucleic acids in the leucocytes and the nucleated red blood cells to label those cells, where since different types of cells may have different binding capabilities to the fluorescent dye, different fluorescence information may be produced. Moreover, since various types of cells may have different sizes, different forward-scattered light information may be produced, and different side-scattered light information may be produced due to different intracellular morphologies or complexities. It may be understood that the flow cytometer may be used to cause the cells to pass through a detection region one by one to collect the information above, and then various types of cells can be distinguished on a dot plot through analysis.

At Step S12, the processed blood sample may be injected into the flow cytometer such that each cell in the blood sample may pass through a detection region of the flow cytometer, and forward-scatted light information, side-scattered light information and fluorescence information may be detected and collected for each cell in the blood sample. In this step, the forward-scatted light information, the side-scattered light information and the fluorescence information of the cells in the blood sample may be acquired from detection data obtained from a single channel of the flow cytometer. It may be understood that in some other embodiments, the forward-scatted light information, the side-scattered light information and the fluorescence information of the cells in the blood sample may be simultaneously acquired during one detection step, i.e. when each cell passes through the detection region of the flow cytometer, the forward-scattered light information, the side-scattered light information and the fluorescence information of the cells in the blood sample may be collected at the same time. Alternatively, the forward-scatted light information, the side-scattered light information and the fluorescence information of the cells in the blood sample may also be acquired by multiple detection steps. For example, the processed blood sample can be divided into two equal portions, where a first portion of the blood sample may be injected into the flow cytometer, the cells in this portion of blood sample can pass through the detection region of the flow cytometer, and the forward-scattered light information and the fluorescence information of each cell in the first portion of blood sample may be detected and collected; and then a second portion of blood sample may be injected into the flow cytometer, the cells in this portion of blood sample can also pass through the detection region of the flow cytometer, and the side-scattered light information and the fluorescence information of each cell in the second portion of blood sample may be detected and collected.

At Step S14, according to the collected side-scattered light information and fluorescence information, a side-scattered light-fluorescence dot plot may be generated for the blood sample, and the leucocytes may be classified into four groups, i.e. a lymphocyte population, a monocyte population, an eosinophil population, and a neutrophil and basophil population.

At Step S16, according to the collected forward-scattered light information and fluorescence information, a forward-scattered light-fluorescence dot plot may be generated for this blood sample, where this dot plot may include a leucocyte population region.

At Step S18, a predetermined feature region of the forward-scattered light-fluorescence dot plot may be acquired, where the predetermined feature region may be located at the left side of the leucocyte population region. After that, statistics may be performed on the amount of characterization cells (i.e. cell particles) in the predetermined feature region of the forward-scattered light-fluorescence information dot plot generated in step S16. It may then be determined whether the amount of the characterization cells exceeds a threshold value, and a warning may be provided when it is determined that the amount of the characterization cells exceeds the threshold value.

It may be understood that the location and the size of the predetermined feature region may be unchanged (i.e. decided in advance), or may be dynamically adjusted as a function of the position of the leucocyte population or a blood shadow region in the forward-scattered light-fluorescence dot plot. In some examples, two forward-scattered light-fluorescence dot plots may be obtained by respectively detecting a normal blood sample containing no nucleated red blood cells and an abnormal blood sample known to contain nucleated red blood cells in the same detection system by means of the above-mentioned method. Through comparison, a region may be found at the left side of the leucocyte population, in which case a particle population appears in this region of the forward-scattered light-fluorescence dot plot of the abnormal blood sample, while no particle population exists in this region of the forward-scattered light-fluorescence dot plot of the normal blood sample. In this way, this region can be determined as the predetermined feature region.

When the location and the size of the predetermined feature region are unchanged, the step S18 may include some sub-steps below.

The amount of the characterization cells in the predetermined feature region may be counted.

The amount of the characterization cells may be compared with a predetermined threshold value. The predetermined threshold value can be a statistical empirical value obtained by experiments. It may also be understood that the predetermined threshold value can be adjusted depending on actual conditions.

When the amount of the characterization cells is greater than the predetermined threshold value, it can be determined that nucleated red blood cells exist in the blood sample, and a warning may then be provided. The warning may include providing a warning prompt in the form of text, sound, light or a pop-up window, etc.

When the location and the size of the predetermined feature region are obtained by means of dynamic adjustment, the step S18 may further determine the predetermined feature region before counting the amount of the characterization cells in the predetermined feature region.

The forward-scattered light-fluorescence dot plot may be analyzed, such that a region located at the left side of the leucocyte population region and at the upper side of the blood shadow region in the forward-scattered light-fluorescence dot plot may be determined as the predetermined feature region.

Figure 12:
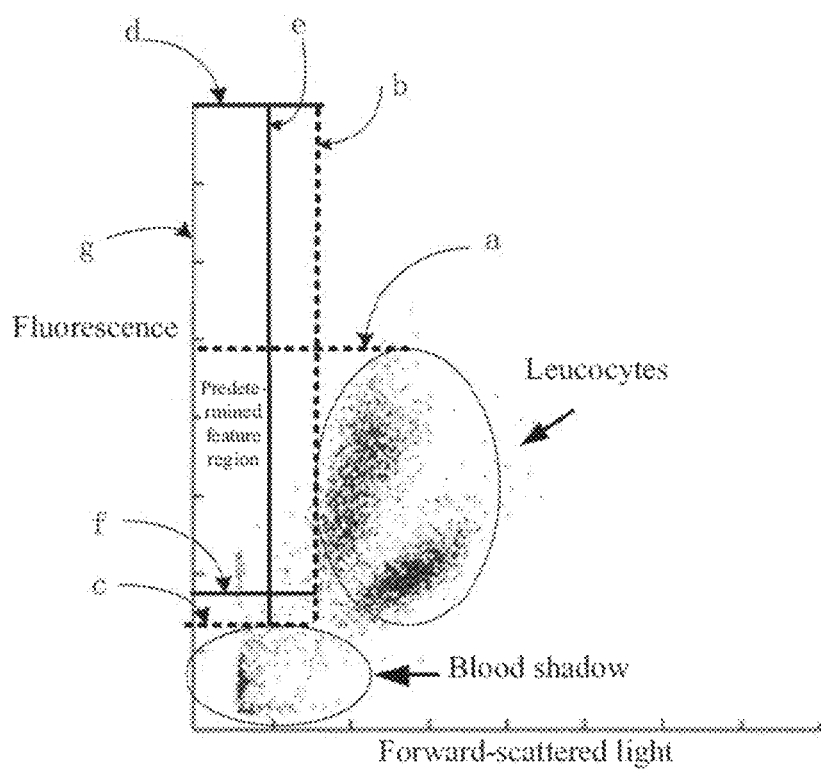
FIG. 12 is a schematic diagram of a predetermined feature region acquired by means of dynamic adjustment.

FIG. 12 shows an example of the predetermined feature region obtained by dynamic adjustment. It can be seen from the forward-scattered light-fluorescence dot plot in FIG. 12 that an upper boundary a of the leucocyte population region, a left boundary b of the leucocyte population region and an upper boundary c of the blood shadow region can be obtained according to position data of the leucocyte population region and position data of the blood shadow region. In some embodiments, the upper boundary a of the leucocyte population region can be taken as an upper boundary of the predetermined feature region, or an upper limit d of fluorescence intensity can be taken as the upper boundary of the predetermined feature region; the left boundary b of the leucocyte population region can be taken as a right boundary of the predetermined feature region, or a line e obtained by moving the left boundary b of the leucocyte population region to the left by some distance can be taken as the right boundary of the predetermined feature region; the upper boundary c of the blood shadow region can be taken as a lower boundary of the predetermined feature region, or a boundary f obtained by moving the upper boundary c of the blood shadow region upwards by some distance can be taken as the lower boundary of the predetermined feature region; and a longitudinal axis g can be designated as a left boundary of the predetermined feature region. Therefore, the size and the location of the predetermined feature region can be determined dynamically according to the upper boundary, the lower boundary, the left boundary and the right boundary of the predetermined feature region. In FIG. 12, the region enclosed by boundaries a (or d), b (or e), c (or f) and the longitudinal axis g can serve as the predetermined feature region. The distance for movement to the left and the distance for movement upwards can be the same or different, and these two distances may be determined in advance.

In some embodiments, a feature region can be pre-stored in the flow cytometer, and the flow cytometer may also pre-store corresponding position data of the leucocyte population region and position data of the blood shadow region. When the forward-scattered light-fluorescence dot plot of the current blood sample is generated, the current position data of the leucocyte population region and the current position data of the blood shadow region may be detected in the forward-scattered light-fluorescence dot plot. When these current position data are different (beyond a preset error range) from corresponding data pre-stored in the flow cytometer, the position of the feature region for warning nucleated red blood cell (i.e. the predetermined feature region) may then be determined according to the current position data of the leucocyte population region and the current position data of the blood shadow region. When the pre-stored region is rectangular, a current feature region for warning nucleated red blood cell can be determined in the way introduced in the preceding paragraph. When the pre-stored region is of another shape such as a circular or oval shape, the current feature region for warning nucleated red blood cell can be determined in some other ways (for example, center shifting method). When the detected position data and the corresponding data pre-stored in the flow cytometer are substantially the same (for example, within a preset error range), the position of the predetermined feature region pre-stored in the system may be taken as the position of the predetermined feature region in the forward-scattered light-fluorescence dot plot of the blood sample, and further calculations can be avoided in this way.

It may be understood that the numbers of the steps above are merely for convenience of expression and do not limit the sequence of the steps.

The term "dot plot" as used herein can be a visualized graph or a set of non-visualized data, as long as it enables the method above to be implemented.

The nucleated red blood cell warning method provided in this disclosure may use a characterization cell population to issue a warning for nucleated red blood cell. When it is capable to classify the leucocytes into four groups using the side-scattered light information and the fluorescence information, a fixedly located region can be found on the forward-scattered light-fluorescence dot plot obtained through corresponding detection (e.g., in a single channel, simultaneously, or in the same detection system), and one cell population within the fixedly located region may be correlated with a clinical diagnosis that whether nucleated red blood cells exist in the detected blood sample; this cell population may be referred to as a characterization cell population of the nucleated red blood cell. Therefore, the characterization cell population can be used to provide a warning for nucleated red blood cells when implementing the classification of the leucocytes. It is concluded without limitation by theory that since nucleated red blood cells may usually appear in the blood samples of patients with a serious disorder such as hemolytic anemia, malignant tumor, erythroleukemia or myelofibrosis, these red blood cells existing in the blood samples may be abnormal in some extent, such as variations in cell membranes. The abnormality may lead to antihemolytic property when a reagent is used, and therefore these red blood cells may produce a weak forward-scattered light signal when passing through a flow cytometer; on the other hand, some constituents of these red blood cells, such as cytochrome or riboflavin, may have non-specific binding with fluorescent dye, and thus these red blood cells may also produce a weak fluorescence signal. In this way, the dots produced by these abnormal red blood cells when passing through the flow cytometer may appear in a specific region of a forward-scattered light-fluorescence dot plot. Accordingly, it may be possible to determine, following clinical significance, whether nucleated red blood cells exist in the blood sample by detecting whether a characterization cell population appears in the specific region of the forward-scattered light-fluorescence dot plot.

In some embodiments of this disclosure, when it is capable to classify the leucocytes into four groups (a lymphocyte population, a monocyte population, an eosinophil population, and a neutrophil and basophil population) on the side-scattered light-fluorescence dot plot, the characterization cell population can be distinguished from the leucocytes when switching to the forward-scattered light-fluorescence dot plot. Two embodiments are provided below for further description for convenience of understanding.

In one embodiment, the steps afore-described in this disclosure can be used to provide warning for nucleated red blood cells, where in the preprocessing of step S10, a first reagent of the following formulation may be used for classifying and counting the leucocytes. Here, the first reagent may include the following constituents:

| Fluorescent dye of structural formula A | 0.5 ppm |
| --- | --- |
| Decyl isoquinolinium bromide | 0.4 g/L |
| Lauryl polyoxyethylene (23) ether | 1.3 g/L |
| Methanol | 50 g/L |
| Sodium dihydrogen phosphate | 3 g/L |
| Disodium hydrogen phosphate | 4.8 g/L |

Structural formula A:

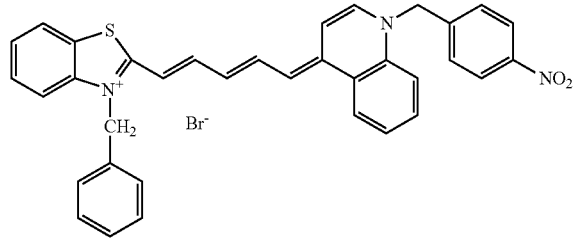 [SMILES: O=[N+]([O-])c1ccc(CN2C=C\C(=C/C=C/C=C/c3sc4ccccc4[n+]3Cc3ccccc3)c3ccccc32)cc1 ; [Br-]]

20 μl anti-coagulated blood of a normal blood sample was added into 1 ml of the above-described first reagent and mixed for 25 seconds under a temperature maintained at about 25° C. 20 μl anti-coagulated blood of a blood sample known to contain nucleated red blood cells (which may be referred to as a nucleated red blood cell blood sample) was added into another 1 ml of the above-described first reagent, and mixed for 25 seconds under a temperature maintained at about 25° C.

Then in step S12, the leucocytes were detected using laser cytometry (light source: red semiconductor laser with a wavelength of about 640 nm). Fluorescence intensity information of cells was detected using side fluorescence with a detection angle of 90°, side-scattered light intensity information of the cells was detected using side-scattered light with a detection angle of 90°, and forward-scattered light information of the cells was detected using forward-scattered light with a detection angle of 2-8°. In this way, the forward-scattered light information, the side-scattered light information and the fluorescence information can be obtained for each cell in the two blood samples, respectively.

Figure 2A:
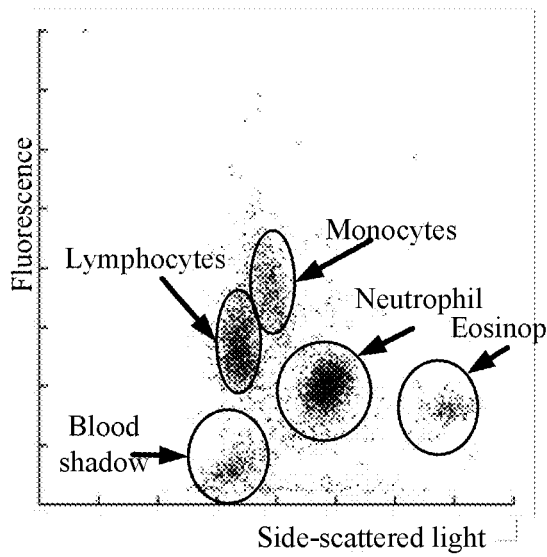
FIG. 2A is a schematic diagram of a side-scattered light-fluorescence dot plot corresponding to a blood sample containing no nucleated red blood cells.
Figure 2B:
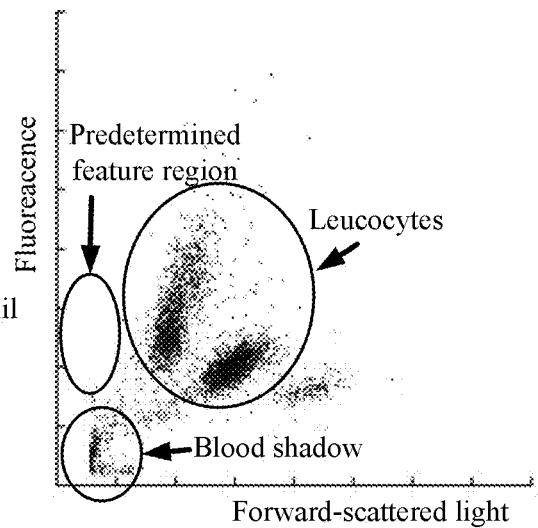
FIG. 2B is a schematic diagram of a forward-scattered light-fluorescence dot plot corresponding to a blood sample containing no nucleated red blood cells.
Figure 3A:
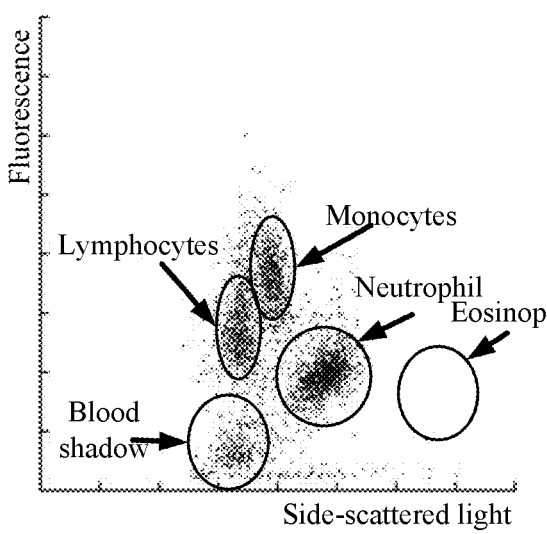
FIG. 3A is a schematic diagram of a side-scattered light-fluorescence dot plot corresponding to a blood sample containing nucleated red blood cells.
Figure 3B:
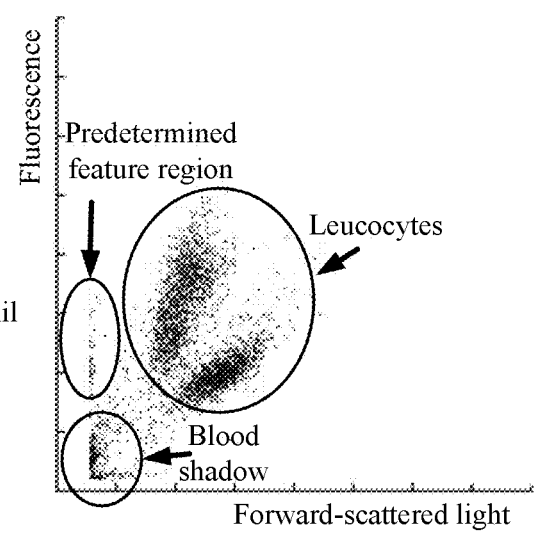
FIG. 3B is a schematic diagram of a forward-scattered light-fluorescence dot plot corresponding to a blood sample containing nucleated red blood cells.

According to the collected side-scattered light information and fluorescence information, a side-scattered light-fluorescence dot plot was generated for the normal blood sample and the nucleated red blood cell blood sample respectively (as shown in FIG. 2A and FIG. 3A), so as to classify the leucocytes into four groups, i.e. a lymphocyte population, a monocyte population, an eosinophil population, and a neutrophil and basophil population. Forward-scattered light-fluorescence dot plots of the two blood samples (as shown in FIG. 2B and FIG. 3B) were generated from the collected forward-scattered light information and fluorescence information, where it can be seen that a characterization cell population (which is considered to be a particle population related to nucleated red blood cells) appears in a specified region of the forward-scattered light-fluorescence dot plot of the nucleated red blood cell blood sample (FIG. 3B). FIG. 4 is a three-dimensional forward-scattered light-fluorescence dot plot of the nucleated red blood cell blood sample, and it can be seen that the characterization cell population related to the nucleated red blood cells appears in a specified region.

In another embodiment, a fluorescent dye B of a different structure was used to formulate a second reagent, where the second reagent may include the following constituents:

| Fluorescent dye of structural formula B | 0.5 ppm |
| --- | --- |
| Tetradecyltrimethylammonium chloride | 0.3 g/L |
| Lauryl polyoxyethylene (23) ether | 1.3 g/L |
| Phthalic acid | 3.0 g/L |
| Tris | 2.4 /L |
| pH value was adjusted to about 7.0 using hydrochloric acid. | |

Structural formula B:

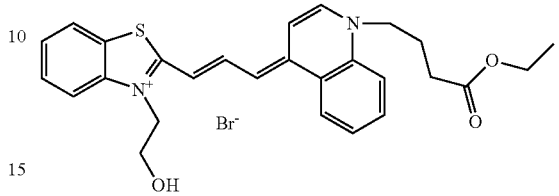

The steps afore-described in this disclosure was also used to provide warning for nucleated red blood cells. In step S10, 20 μl anti-coagulated blood of a normal blood sample was added into 1 ml of the above-described second reagent and mixed for 25 seconds under a temperature maintained at about 25° C. 20 μl anti-coagulated blood of a blood sample known to contain nucleated red blood cells (which may be referred to as a nucleated red blood cell blood sample) was added into another 1 ml of the above-described second reagent, and mixed for 25 seconds under a temperature maintained at about 25° C.

Then in step S12, the leucocytes were detected using laser cytometry (light source: red semiconductor laser with a wavelength of about 640 nm). Fluorescence intensity information of cells was detected using side fluorescence with a detection angle of 90°, side-scattered light intensity information of the cells was detected using side-scattered light with a detection angle of 90°, and forward-scattered light information of the cells was detected using forward-scattered light with a detection angle of 2-8°. In this way, the forward-scattered light information, the side-scattered light information and the fluorescence information can be obtained for each cell in the two blood samples.

Figures 6A, 6B:
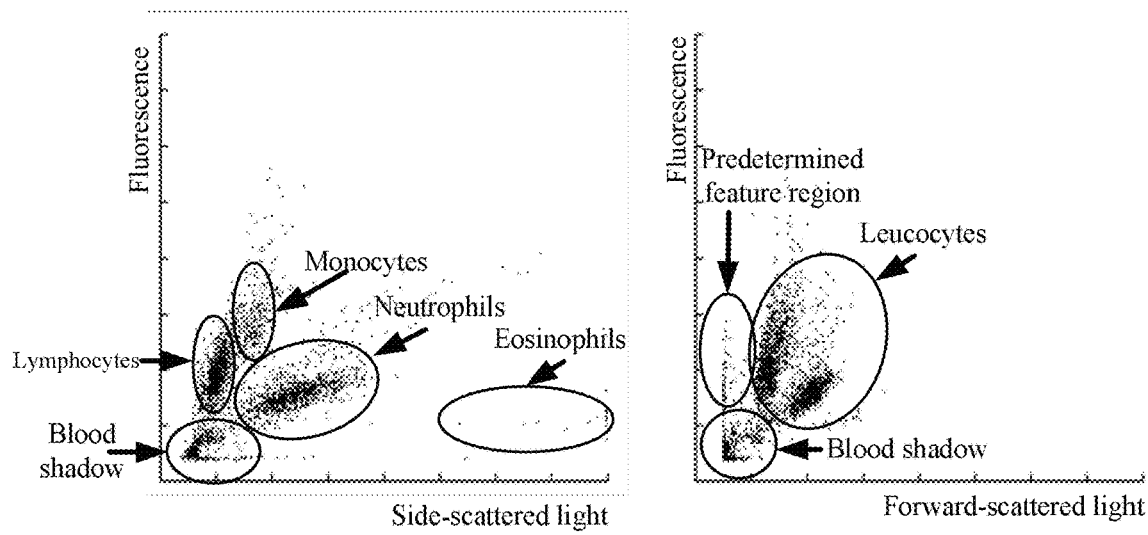
FIG. 6A is a schematic diagram of a side-scattered light-fluorescence dot plot corresponding to a blood sample containing nucleated red blood cells.
FIG. 6B is a schematic diagram of a forward-scattered light-fluorescence dot plot corresponding to a blood sample containing nucleated red blood cells.
Figure 7:
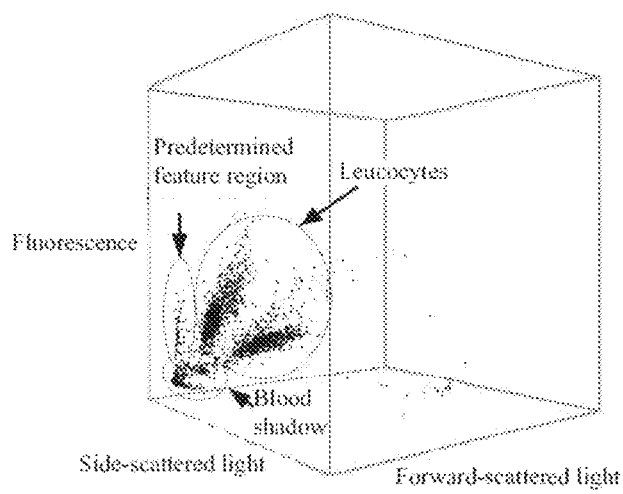
FIG. 7 is a schematic diagram of a three-dimensional dot plot corresponding to FIG. 6A and FIG. 6B.

According to the collected side-scattered light information and fluorescence information, a side-scattered light-fluorescence dot plot was generated for the normal blood sample and the nucleated red blood cell blood sample respectively (as shown in FIG. 5A and FIG. 6A), so as to classify the leucocytes into four groups, i.e. a lymphocyte population, a monocyte population, an eosinophil population, and a neutrophil and basophil population. Forward-scattered light-fluorescence dot plots of the two blood samples (as shown in FIG. 5B and FIG. 6B) were generated from the collected forward-scattered light information and fluorescence information, where it can be seen that a characterization cell population (which is considered to be a particle population related to nucleated red blood cells) appears in a specified region of the forward-scattered light-fluorescence dot plot of the nucleated red blood cell blood sample (FIG. 6B). FIG. 7 is a three-dimensional forward-scattered light-fluorescence dot plot of the nucleated red blood cell blood sample, and it can be seen that the characterization cell population related to the nucleated red blood cells appears in a specified region.

It can be seen from the two embodiments above that even different reagents were used in the preprocessing step, the characterization cell population can both appear in the specified region.

It may be understood that the method of the embodiments of this disclosure can be implemented by a flow cytometer and a CPU of the flow cytometer, or by means of software operated by the flow cytometer. Moreover, it may be understood that the method provided in the embodiments of this disclosure are not directly associated with the used reagent. As long as the leucocytes can be classified into four groups in the side-scattered light-fluorescence dot plot, a feature region can then be found above a blood shadow and/or at the left side of a leucocyte region in the forward-scattered light-fluorescence dot plot generated by the forward-scattered light information and fluorescence information.

In order to further confirm the effect of the nucleated red blood cell warning method provided in the embodiments of this disclosure, some comparative experiments are performed. 1229 blood samples were collected, and manual microscopy was performed on the blood samples using the H20-A2 method recommended by the CLSI (Clinical and Laboratory Standards Institute). In accordance with a criteria about positive microscopy made by the International Consensus Group for Hematology Review, the microscopy results were determined as positive if NRBC≥1% during manual microscopy of a blood smear, and otherwise, the microscopy results were determined as negative. Among these 1229 samples, 131 samples were positive samples (i.e. the ratio of nucleated red blood cells to leucocytes contained therein was greater than or equal to 1%), and 1098 samples were negative samples.

The flow cytometer was also used to detect those 1229 blood samples, and the method provided in the embodiments of this disclosure was used to provide a warning for the samples that may contain nucleated red blood cells therein. The warning information was issued for 180 samples, and no warning was provided for 1049 samples.

Then each sample that is warned to contain nucleated red blood cells was compared with the manual microscopy result. The comparison showed that in the 180 warned samples, 117 were positive samples and 63 were negative samples; and in the 1049 non-warned samples, 14 were positive samples and 1035 were negative samples. Specific comparison results are as shown in Table 1.

TABLE 1

Comparison of warned result using method provided in the embodiments of this disclosure with manual microscopy results

| Microscopy results | | Results of nucleated red blood cell warning using the method of this disclosure | | | |
|---|---|---|---|---|---|
| Positive | Negative | Number of true positives | Number of true negatives | Number of false positives | Number of false negatives |
| 131 | 1098 | 117 | 1035 | 63 | 14 |
| | | True positive rate 89.31% | True negative rate 94.26% | False positive rate 5.74% | False negative rate 10.69% |

The true positive rate, the true negative rate, the false negative rate and the false positive rate were obtained using the following calculation formulae:

true positive rate=number of true positives/(number of true positives+number of false negatives)*100%;

true negative rate=number of true negatives/(number of true negatives+number of false positives)*100%;

false positive rate=number of false positives/(number of true negatives+number of false positives)*100%;

false negative rate=number of false negatives/(number of true positives+number of false negatives)*100%.

The results above show that using the method provided in the embodiments of this disclosure to detect nucleated red blood cells in a blood sample provides a relatively high warning sensitivity and specificity, and good warning accuracy.

Figure 8:
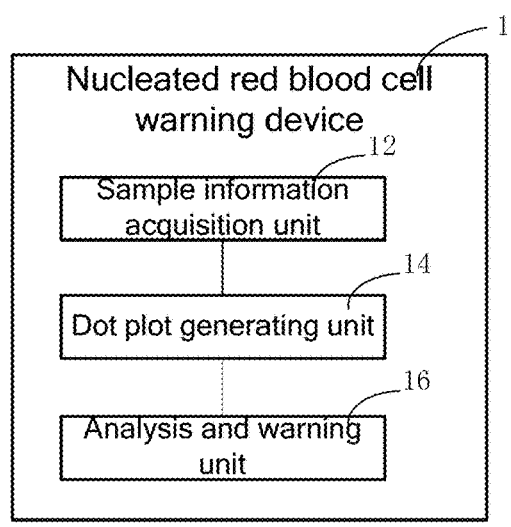
FIG. 8 is a schematic diagram of a nucleated red blood cell warning device.
Figure 9:
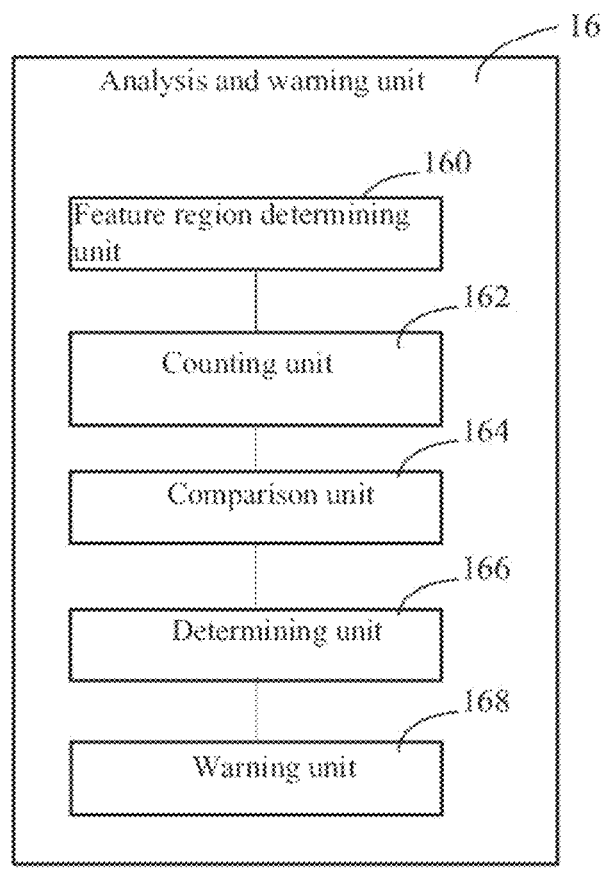
FIG. 9 is a schematic diagram of an analysis and warning unit in FIG. 8.

In some embodiments of this disclosure, a nucleated red blood cell warning device can be provided. FIG. 8 to FIG. 9 show an embodiment of a nucleated red blood cell warning device. In this embodiment, the nucleated red blood cell warning device 1 may be used for warning whether nucleated red blood cells exist in a blood sample. The nucleated red blood cell warning device 1 may include a sample information acquisition unit 12, a dot plot generating unit 14 and an analysis and warning unit 16.

The sample information acquisition unit 12 may acquire forward-scattered light information, side-scattered light information and fluorescence information when cells in the blood sample pass through a detection region of a flow cytometer. In some embodiments, the sample information acquisition unit 12 may acquire the forward-scattered light information, the side-scattered light information and the fluorescence information of the cells in the blood sample from detection data obtained from a single channel.

The dot plot generating unit 14 may generate a side-scattered light-fluorescence dot plot according to the side-scattered light information and the fluorescence information acquired by the sample information acquisition unit 12 so as to classify leucocytes into at least four groups, i.e. a lymphocyte population, a monocyte population, an eosinophil population, and a neutrophil and basophil population. The dot plot generating unit 14 may also generate a forward-scattered light-fluorescence dot plot of the blood sample according to the forward-scattered light information and the fluorescence information acquired by the sample information acquisition unit 12, where the forward-scattered light-fluorescence dot plot may include a leucocyte population region.

The analysis and warning unit 16 may acquire a predetermined feature region of the forward-scattered light-fluorescence dot plot, perform statistics on the amount of characterization cells in the predetermined feature region, determine whether the amount of the characterization cells exceeds a threshold value, and provide a warning when it is determined that the amount of the characterization cells exceeds the threshold value. Here, the predetermined feature region is located at the left side of the leucocyte population.

The analysis and warning unit 16 may include a feature region determining unit 160, a counting unit 162, a comparison unit 164, a determining unit 166 and a warning unit 168.

The feature region determining unit 160 may analyze the forward-scattered light-fluorescence dot plot, and determine a region located at the left side of the leucocyte population region and at an upper side of a blood shadow region in the forward-scattered light-fluorescence dot plot as the predetermined feature region.

The counting unit 162 may count the amount of the characterization cells in the predetermined feature region.

The comparison unit 164 may compare the amount of the characterization cells with a predetermined threshold value.

The determining unit 166 may determine that nucleated red blood cells exist in the blood sample when the amount of the characterization cells is greater than the predetermined threshold value.

The warning unit 168 may provide a warning when it is determined that nucleated red blood cells exist in the blood sample. The warning may include warning prompt in the form of text, sound, light or a pop-up window, etc.

It may be understood that if the location and the size of the predetermined feature region are unchanged, the analysis and warning unit 16 may not include the feature region determining unit 160.

For more detail, reference can also be made to the description above with respect to FIG. 1 to FIG. 7, which will not be repeated here.

Figure 10:
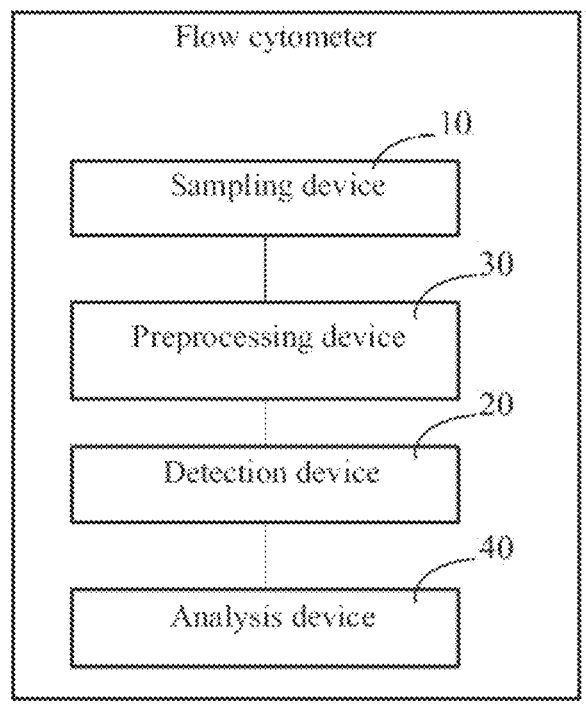
FIG. 10 is a schematic diagram of a flow cytometer.

FIG. 10 is a structural schematic diagram of a detection device in a flow cytometer provided by this disclosure. The flow cytometer may include a sampling device 10, a prepossessing device 30, a detection device 20 and an analysis device 40.

The sampling device 10 may draw a blood sample containing leucocytes.

The preprocessing device 30 may preprocess the blood sample so as to obtain a processed blood sample, where the preprocessing may at least include performing fluorescence labeling on cells in the blood sample.

The detection device 20 may cause the cells in the processed blood sample to pass through a detection region one by one, and detect forward-scattered light information, side-scattered light information and fluorescence information of the cells in the blood sample. In some embodiments, the detection device 20 may detect and collect the forward-scattered light information, the side-scattered light information and the fluorescence information of the cells in the blood sample from a single channel.

The analysis device 40 may generate a forward-scattered light-fluorescence dot plot of the blood sample according to the forward-scattered light information, the side-scattered light information and the fluorescence information detected by the detection device, acquire a predetermined feature region of the forward-scattered light-fluorescence dot plot, perform statistics on the amount of characterization cells in the predetermined feature region, determine whether the amount of the characterization cells exceeds a threshold value, and provide a warning when it is determined that the amount of the characterization cells exceeds the threshold value. Here, the forward-scattered light-fluorescence dot plot may include a leucocyte population region, and the predetermined feature region may be located at the left side of the leucocyte population region, where the location and the size of the predetermined feature region may be fixed or dynamically set.

The analysis device 40 can be implemented in a CPU, and can include the nucleated red blood cell warning device 1 as described previously with respect to FIG. 8 and FIG. 9. For more detail, reference can be made to the aforementioned descriptions of FIG. 8 and FIG. 9.

Figure 11:
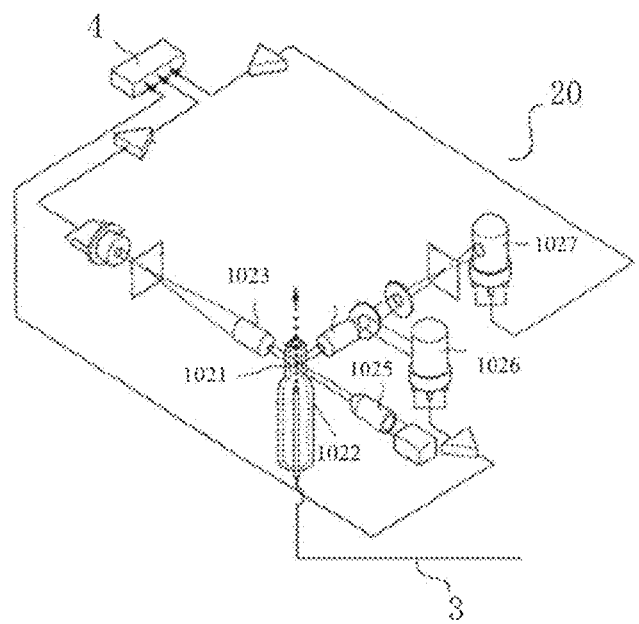
FIG. 11 is a structure diagram of a detection device in FIG. 10.

FIG. 11 shows a schematic structural diagram of the detection device 20 in FIG. 10. It can be seen therefrom that the detection device 20 can include: a light source 1025, a flow chamber 1022 serving as the detection region, a forward-scattered light collection device 1023 provided on an optical axis, and a side-scattered light collection device 1026 and a side-scattered fluorescence collection device 1027 provided by a side of the optical axis. The cells of the blood sample processed by the preprocessing device 30 may successively enter the flow chamber 1022 (the detection region) via a tube 3, where the forward-scattered light collection device 1023, the side-scattered light collection device 1026 and the side-scattered fluorescence collection device 1027 in the same channel may successively detect and collect the forward-scattered light, the side-scattered light and the side-scattered fluorescence information of each cell, and may transmit these information to the analysis device 40 via a communication interface 4.

For more detail, reference can also be made to the description above with respect to FIG. 1 to FIG. 9, which details will not be repeated here.

In the embodiments of this disclosure, the blood sample is preprocessed using the reagent and the cells in the blood sample are detected by the flow cytometer so as to obtain the side-scattered light, the forward-scattered light and the fluorescence information of the cells. The leucocytes in the blood sample can be classified into four groups by forming the side-scattered light-fluorescence dot plot according to the detected information, on one hand. On the other hand, the specific region at the left side of the leucocyte population region of the dot plot can be counted and analyzed by forming the forward-scattered light-fluorescence dot plot, so as to enable a function of nucleated red blood cell warning. That is, both functions of warning for nucleated red blood cells and classification of leucocytes into four groups can be implemented by means of measurement in a single channel.

In the embodiments of this disclosure, a warning for nucleated red blood cells can be provided while classifying and detecting leucocytes without using specialized nucleated red blood cell reagent and without counting the amount of the nucleated red blood cell, whereby information for clinical screening can be provided quickly, simply and conveniently without increasing complexity and costs of the measurement.

A person ordinarily skilled in the art will understand that all or part of the processes of the methods in the embodiments above can be implemented through instructing related hardware by programs of a computer. The programs can be stored in a computer readable storage medium. When the programs are being executed, the processes as described in the embodiments above may be implemented. The storage medium may be disk, CD, ROM (Read-Only Memory) or RAM (Random Access Memory), etc.

The technical features or operation steps illustrated in the embodiments of this disclosure can be combined in any way. Those of ordinary skilled persons in the art may easily understand that the sequence of steps or actions in the methods illustrated by the embodiments of this disclosure can be altered. Therefore, unless a certain sequence is specified otherwise, any sequence in the figures or the detailed description is merely for the purpose of illustration and not an obligatory sequence.

The descriptions above are merely preferred implementations of this disclosure and should not be taken as limiting of the claimed scope of this disclosure. Therefore, any equivalent changes made to the claims of this disclosure remain within the scope covered by this disclosure.

The invention claimed is:

1. A nucleated red blood cell warning method for warning whether nucleated red blood cells exist in a blood sample, comprising:

preprocessing the blood sample to obtain a processed blood sample, wherein the preprocessing comprises mixing the blood sample with a reagent containing a fluorescent dye and a hemolytic component to form the processed blood sample, the hemolytic component hemolyzes red blood cells in the blood sample, and the fluorescent dye binds with nucleic acids in leucocytes and the nucleated red blood cells in the blood sample;

acquiring forward-scattered light information, side-scattered light information and fluorescence information when cells in the processed blood sample pass through a detection region of a flow cytometer;

classifying, according to said side-scattered light information and said fluorescence information, the leucocytes into at least four groups comprising: a lymphocyte population, a monocyte population, an eosinophil population, and a neutrophil and basophil population;

generating, according to said forward-scattered light information and said fluorescence information, a forward-scattered light-fluorescence dot plot of said blood sample, wherein an X axis of the said forward-scattered light-fluorescence dot plot represents the forward-scattered light information, and a Y axis of the said forward-scattered light-fluorescence dot plot represents the fluorescence information, wherein said forward-scattered light-fluorescence dot plot comprises a leucocyte population region; and acquiring a predetermined feature region of said forward-scattered light-fluorescence dot plot, performing statistics on an amount of characterization cells in said predetermined feature region, determining whether said amount of said characterization cells exceeds a predetermined threshold value, and providing a warning when it is determined that said amount of said characterization cells exceeds said predetermined threshold value, wherein said predetermined feature region is located at a left side of said leucocyte population region.

2. The nucleated red blood cell warning method of claim 1, wherein performing statistics on said amount of said characterization cells in said predetermined feature region, determining whether said amount of said characterization cells exceeds said predetermined threshold value, and providing said warning when it is determined that said amount of said characterization cells exceeds said predetermined threshold value comprise:

counting said amount of said characterization cells in said predetermined feature region;

comparing said amount of said characterization cells with said predetermined threshold value; and determining that nucleated red blood cells exist in said blood sample when said amount of said characterization cells is greater than said predetermined threshold value, and providing said warning when it is determined that nucleated red blood cells exist in said blood sample.

3. The nucleated red blood cell warning method of claim 1, wherein acquiring said predetermined feature region of said forward-scattered light-fluorescence dot plot comprises:
analyzing said forward-scattered light-fluorescence dot plot and determining a region located at the left side of said leucocyte population region and at an upper side of a blood shadow region in said forward-scattered light-fluorescence dot plot as said predetermined feature region.

4. The nucleated red blood cell warning method of claim 1, wherein acquiring said forward-scattered light information, said side-scattered light information and said fluorescence information when said cells in the processed blood sample pass through said detection region of said flow cytometer comprises acquiring said forward-scattered light information, said side-scattered light information and said fluorescence information of said cells in the processed blood sample from detection data obtained from a single channel.

5. The nucleated red blood cell warning method of claim 1, wherein said warning comprises providing a warning prompt in a form of text, sound, light or pop-up window.

6. The nucleated red blood cell warning method of claim 1, wherein the characterization cells are not nucleated red blood cells, but are capable of indicating presence of nucleated red blood cells.

7. The nucleated red blood cell warning method of claim 1, wherein the predetermined feature region is obtained by dynamic adjustment as a function of a position of the leucocyte population region in the forward-scattered light-fluorescence dot plot.

8. The nucleated red blood cell warning method of claim 1, wherein the predetermined feature region, corresponding position data of the leucocyte population region, and position data of a blood shadow region are pre-stored in the flow cytometer, when the forward-scattered light-fluorescence dot plot of current blood sample is generated, current position data of the leucocyte population region and current position data of the blood shadow region are detected, when the current position data of the leucocyte population region and/or the current position data of the blood shadow region are different from the corresponding position data of the leucocyte population region and/or the position data of the blood shadow region pre-stored in the flow cytometer, the position of the predetermined feature region is dynamic adjusted according to the current position data of the leucocyte population region and the current position data of the blood shadow region.

9. The nucleated red blood cell warning method of claim 1, wherein the predetermined feature region is obtained by dynamic adjustment as a function of a position of the leucocyte population region and a position of a blood shadow region in the forward-scattered light-fluorescence dot plot.

10. A nucleated red blood cell warning device for warning whether nucleated red blood cells exist in a blood sample, comprising a processor, wherein said processor is configured to:

acquire forward-scattered light information, side-scattered light information and fluorescence information when cells in a processed blood sample pass through a detection region of a flow cytometer, wherein the processed blood sample is obtained by preprocessing the blood sample, wherein the preprocessing comprises mixing the blood sample with a reagent containing a fluorescent dye and a hemolytic component to form the processed blood sample, the hemolytic component hemolyzes red blood cells in the blood sample, and the fluorescent dye binds with nucleic acids in leucocytes and the nucleated red blood cells in the blood sample;

generate a side-scattered light-fluorescence dot plot according to said side-scattered light information and said fluorescence information and classify the leucocytes into at least four groups comprising: a lymphocyte population, a monocyte population, an eosinophil population, and a neutrophil and basophil population;

generate a forward-scattered light-fluorescence dot plot of the processed blood sample according to said forward-scattered light information and said fluorescence information, wherein an X coordinate axis of the said forward-scattered light-fluorescence dot plot represents the forward-scattered light information, and a Y coordinate axis of the said forward-scattered light-fluorescence dot plot represents the fluorescence information, wherein said forward-scattered light-fluorescence dot plot comprises a leucocyte population region; and acquire a predetermined feature region of said forward-scattered light-fluorescence dot plot, perform statistics on an amount of characterization cells in said predetermined feature region, determine whether said amount of said characterization cells exceeds a predetermined threshold value, and provide a warning when it is determined that said amount of said characterization cells exceeds said predetermined threshold value, wherein said predetermined feature region is located at a left side of said leucocyte population region.

11. The nucleated red blood cell warning device of claim 10, wherein said processor is further configured to: analyze said forward-scattered light-fluorescence dot plot and determine a region located at the left side of said leucocyte population region and at an upper side of a blood shadow region in said forward-scattered light-fluorescence dot plot as said predetermined feature region.

12. The nucleated red blood cell warning device of claim 10, wherein said processor is further configured to:
count said amount of said characterization cells in said predetermined feature region;
compare said amount of said characterization cells with said predetermined threshold value;
determine that nucleated red blood cells exist in said blood sample when said amount of said characterization cells is greater than said predetermined threshold value; and
provide said warning when it is determined that nucleated red blood cells exist in said blood sample.

13. The nucleated red blood cell warning device of claim 10, wherein said processor is further configured to acquire said forward-scattered light information, said side-scattered light information and said fluorescence information of said cells in the processed blood sample from detection data obtained from a single channel.

14. The nucleated red blood cell warning device of claim 10, wherein the characterization cells are not nucleated red blood cells, but are capable of indicating presence of nucleated red blood cells.

15. A flow cytometer, comprising: a sampling device that draws a blood sample, said blood sample containing at least leucocytes;
a preprocessing device that preprocesses said blood sample to obtain a processed blood sample, said preprocessing comprising mixing the blood sample with a reagent containing a fluorescent dye and a hemolytic component to form the processed blood sample, the hemolytic component hemolyzes red blood cells in the blood sample, and the fluorescent dye binds with nucleic acids in the leucocytes and nucleated red blood cells in the blood sample;
a detection device that causes cells in said processed blood sample to pass through a detection region one by one, and detects forward-scattered light information, side-scattered light information and fluorescence information of said cells in said processed blood sample; and
an analysis device that generates a side-scattered light-fluorescence dot plot according to said side-scattered light information and said fluorescence information, classifies said leucocytes of said blood sample into at least four groups comprising: a lymphocyte population, a monocyte population, an eosinophil population, and a neutrophil and basophil population, generates a forward-scattered light-fluorescence dot plot of said blood sample according to said forward-scattered light information and said fluorescence information detected by said detection device, acquires a predetermined feature region of said forward-scattered light-fluorescence dot plot, performs statistics on an amount of characterization cells in said predetermined feature region, determines whether said amount of said characterization cells exceeds a predetermined threshold value, and provides a warning when it is determined that said amount of said characterization cells exceeds said predetermined threshold value, wherein an X coordinate axis of the said forward-scattered light-fluorescence dot plot represents the forward-scattered light information, and a Y coordinate axis of the said forward-scattered light-fluorescence dot plot represents the fluorescence information, wherein said forward-scattered light-fluorescence dot plot comprises a leucocyte population region and said predetermined feature region is located at a left side of said leucocyte population region.

16. The flow cytometer of claim 15, wherein said analysis device is further configured to: analyze said forward-scattered light-fluorescence dot plot and determine a region located at the left side of said leucocyte population region and at an upper side of a blood shadow region in said forward-scattered light-fluorescence dot plot as said predetermined feature region.

17. The flow cytometer of claim 15, wherein said detection device detects and collects said forward-scattered light information, said side-scattered light information and said fluorescence information of said cells in said blood sample using a single channel.

18. The flow cytometer of claim 15, wherein the characterization cells are not nucleated red blood cells, but are capable of indicating presence of nucleated red blood cells.

19. A nucleated red blood cell warning method for warning whether nucleated red blood cells exist in a blood sample, comprising: providing a flow cytometer and a blood sample containing leucocytes;
preprocessing said blood sample so as to obtain a processed blood sample, said preprocessing comprising mixing the blood sample with a reagent containing a fluorescent dye and a hemolytic component to form the processed blood sample, the hemolytic component hemolyzes red blood cells in the blood sample, and the fluorescent dye binds with nucleic acids in the leucocytes and the nucleated red blood cells in the blood sample;
injecting said processed blood sample into said flow cytometer, and collecting forward-scattered light information, side-scattered light information and fluorescence information of said cells;
classifying, according to said side-scattered light information and said fluorescence information, said leucocytes into at least four groups comprising: a lymphocyte population, a monocyte population, an eosinophil population, and a neutrophil and basophil population;
generating, according to said forward-scattered light information and said fluorescence information, a forward-scattered light-fluorescence dot plot of said blood sample, said forward-scattered light-fluorescence dot plot comprising a leucocyte population region; and
acquiring a predetermined feature region of said forward-scattered light-fluorescence dot plot, performing statistics on an amount of characterization cells in said predetermined feature region, determining whether said amount of said characterization cells exceeds a predetermined threshold value, and providing a warning when it is determined that said amount of said characterization cells exceeds said predetermined threshold value, wherein an X coordinate axis of the said forward-scattered light-fluorescence dot plot represents the forward-scattered light information, and a Y coordinate axis of the said forward-scattered light-fluorescence dot plot represents the fluorescence information, wherein said predetermined feature region is located at a left side of said leucocyte population region.

20. The nucleated red blood cell warning method of claim 19, wherein performing statistics on said amount of said characterization cells in said predetermined feature region, determining whether said amount of said characterization cells exceeds said predetermined threshold value, and providing said warning when it is determined that said amount of said characterization cells exceeds said predetermined threshold value comprise:
   counting said amount of said characterization cells in said predetermined feature region;
   comparing said amount of said characterization cells with said predetermined threshold value; and
   determining that nucleated red blood cells exist in said blood sample when said amount of said characterization cells is greater than said predetermined threshold value, and providing said warning when it is determined that nucleated red blood cells exist in said blood sample.

21. The nucleated red blood cell warning method of claim 19, wherein injecting said processed blood sample into said flow cytometer, and collecting said forward-scattered light information, said side-scattered light information and said fluorescence information of said cells in said blood sample comprise: simultaneously collecting said forward-scattered light information, said side-scattered light information and said fluorescence information of said cells in said blood sample when said cells pass through said detection region of said flow cytometer.

22. The nucleated red blood cell warning method of claim 19, wherein acquiring said predetermined feature region of said forward-scattered light-fluorescence dot plot comprises: analyzing said forward-scattered light-fluorescence dot plot and determining a region located at the left side of said leucocyte population region and at an upper side of a blood shadow region in said forward-scattered light-fluorescence dot plot as said predetermined feature region.

23. The nucleated red blood cell warning method of claim 19, wherein acquiring said predetermined feature region of said forward-scattered light-fluorescence dot plot comprises:
providing a normal blood sample and an abnormal blood sample, said normal blood sample containing at least leucocytes, and said abnormal blood sample containing at least leucocytes and nucleated red blood cells;
   preprocessing said normal blood sample and said abnormal blood sample so as to obtain a processed normal blood sample and a processed abnormal blood sample, said preprocessing comprising respectively performing fluorescent labeling on cells in said normal blood sample and said abnormal blood sample;
   injecting said processed normal blood sample and said processed abnormal blood sample respectively into said flow cytometer, collecting said forward-scattered light information, said side-scattered light information and said fluorescence information of said cells respectively in said processed normal blood sample and said processed abnormal blood sample;
   classifying, according to said side-scattered light information and said fluorescence information, said leucocytes respectively in said processed normal blood sample and said processed abnormal blood sample into at least four groups: lymphocyte population, monocyte population, eosinophil population, and neutrophil and basophil population;
   generating, according to said forward-scattered light information and said fluorescence information, a forward-scattered light-fluorescence dot plot of said processed normal blood sample and a forward-scattered light-fluorescence dot plot of said processed abnormal blood sample; and
   comparing said forward-scattered light-fluorescence dot plot of said processed normal blood sample and said forward-scattered light-fluorescence dot plot of said processed abnormal blood sample so as to determine a region where a particle population appears at the left side of a leucocyte population region in said forward-scattered light-fluorescence dot plot of said processed abnormal blood sample and where no particle population appears at the left side of a leucocyte population region in said forward-scattered light-fluorescence dot plot of said processed normal blood sample, as said predetermined feature region.

24. The nucleated red blood cell warning method of claim 19, wherein the characterization cells are not nucleated red blood cells, but are capable of indicating presence of nucleated red blood cells.

* * * * *